United States Patent [19]

Omstead et al.

[11] Patent Number: 5,188,944
[45] Date of Patent: Feb. 23, 1993

[54] PROCESS FOR THE GLYCOSYLATION OF AVERMECTIN AGYLCONES

[75] Inventors: Mary N. Omstead, Gladstone; Marvin D. Schulman, Scotch Plains; Noel M. Young, Rahway, all of N.J.

[73] Assignee: Merck & Co., Inc., Rahway, N.J.

[21] Appl. No.: 762,183

[22] Filed: Sep. 19, 1991

Related U.S. Application Data

[63] Continuation-in-part of Ser. No. 542,343, Jun. 22, 1990, abandoned.

[51] Int. Cl.$^5$ .................. C12P 19/62; C12P 19/60; C12R 1/465
[52] U.S. Cl. ........................ 435/76; 435/75; 435/253.5; 435/886; 514/30; 536/7.1
[58] Field of Search ................ 435/75, 76, 886, 253.5; 536/7.1; 514/30

[56] References Cited

U.S. PATENT DOCUMENTS

| | | |
|---|---|---|
| 3,950,360 | 4/1976 | Aoki et al. . |
| 4,156,720 | 5/1979 | Fisher et al. . |
| 4,171,314 | 10/1979 | Chabala et al. . |
| 4,201,861 | 5/1980 | Mrozik et al. . |
| 4,203,976 | 5/1980 | Fisher et al. . |
| 4,206,205 | 6/1980 | Mrozik et al. . |
| 4,289,760 | 9/1981 | Mrozik et al. . |
| 4,310,519 | 1/1982 | Albers-Schonberg et al. . |
| 4,328,335 | 5/1982 | Mrozik . |
| 4,333,925 | 6/1982 | Buhs . |
| 4,378,353 | 3/1983 | Goegelman et al. . |

FOREIGN PATENT DOCUMENTS

| | | |
|---|---|---|
| 214731 | 3/1987 | European Pat. Off. . |
| 277916 | 8/1988 | European Pat. Off. . |
| 188460 | 10/1979 | New Zealand . |
| 191087 | 7/1984 | New Zealand . |
| 197860 | 12/1984 | New Zealand . |
| 191088 | 7/1988 | New Zealand . |
| 199666 | 8/1988 | New Zealand . |
| 216980 | 10/1988 | New Zealand . |
| 2167751 | 6/1986 | United Kingdom . |

OTHER PUBLICATIONS

Streicher, S. L., et al., Cloning Genes for Avermectin Biosynthesis in *Streptomyces avermitilis* Amer. Soc. for Microbiol. pp. 44–52.

*Primary Examiner*—Herbert J. Lilling
*Attorney, Agent, or Firm*—David L. Rose; Joseph F. DiPrima

[57] ABSTRACT

Avermectin aglycones are glycosylated by fermentation in a medium of a non-producing mutant of *Streptomyces avermitilis* MA-6078. The glycosylation produces the monosaccharide and disaccharide derivatives while leaving the remainder of the molecule intact. The microorganism glycosylates with the α-L-oleandrose moiety.

14 Claims, No Drawings

PROCESS FOR THE GLYCOSYLATION OF AVERMECTIN AGYLCONES

CROSS REFERENCE TO RELATED APPLICATIONS

This application is a continuation-in-part of our co-pending application Ser. No. 542343 filed Jun. 22, 1990 and is now abandoned.

BACKGROUND OF THE INVENTION

The avermectin series of compounds (formerly referred to as C-076 compounds) are derived from the natural products disclosed in U.S. Pat. No. 4,310,519 to Albers-Schonberg et. al. and the milbemycin series of compounds as derived from the natural products disclosed in U.S. Pat. No. 3,950,360 to Aoki et. al. The aglycone derivatives of the avermectin compounds are disclosed in U.S. Pat. No. 4,206,205 to Mrozik et. al. Other aglycone compounds with modified C-25 substituents are disclosed in EP 277916 (microbiologically produced) and UK 2167751 (synthetically produced). Avermectin compounds with a variety of 25-position substituents are disclosed in EPO 214731 and such compounds can be readily converted into the corresponding aglycones, which are starting materials for the instant process, following the procedures of U.S. Pat. No. 4,206,205 to Mrozik et al. Synthetic procedures are available for the glycosylation of avermectin compounds which are disclosed in U.S. Pat. No. 4,156,720 to Fisher et. al. and U.S. Pat. No. 4,205,967 to Fisher et. al. Such glycosylation procedures are generally non-selective and require the extensive use of protecting groups to ensure glycosylation at the desired position. The instant process is a selective procedure for the production of 13-mono-and di-glycosylated derivatives of avermectin aglycone compounds.

SUMMARY OF THE INVENTION

The instant invention is concerned with the selective preparation of mono- and disaccharide derivatives from avermectin aglycones by fermention, in a fermentation medium with a mutant of Streptomyces avermitilis, MA-6078. Thus, it is an object of the instant invention to describe the fermentation process. It is a further object of this invention to describe the novel S. avermitilis microorganism. A still further object is to describe the various media that are suitable for the fermentation. Still further objects will be apparent from a reading of the following description.

DESCRIPTION OF THE INVENTION

This invention is concerned with the preparation of avermectin mono- and disaccharides by adding to the fermentation medium of Streptomyces avermitilis MA-6078, a quantity of an avermectin aglycone. S. avermitilis MA-6078 is a novel mutant strain of S. avermitilis with the characteristic that it does not produce any avermectin compounds. Since S. avermitilis is the producing strain for avermectin compounds (See Albers-Schonberg et. al.) this is a significant characteristic which differs S. avermitilis MA-6078 from other S. avermitilis strains.

Thus, S. avermitilis MA-6078 is a novel microorganism and has been deposited under the Budapest Treaty at The American Type Culture Collection at 12301 Parklawn Drive, Rockville, MD 20852 under the accession number ATCC 55017.

The morphological and cultural characteristics of Streptomyces avermitilis: MA-6078, ATCC 55017 are as follows:

The following is a general description of Streptomyces avermitilis strain MA6078. Observations of growth, general cultural characteristics and carbon source utilization were made in accordance with the methods of Shirling and Gottleib (Internat. J. System. Bacteriol. 16: 313–340). Chemical composition of the cells was determined using the methods of Lechevalier and Lechevalier (in Actinomycete Taxonomy, A. Dietz and D. W. Thayer, Ed. Society for Industrial Microbiology, 1980). Coloration of the culture was determined by comparison with color standards contained in the Inter-Society Color Council-National Bureau of Standards Centroid Color Charts (US Dept. of Commerce National Bureau of Standards supplement to NBS Circular 553, 1985).

Source-The culture was derived from Streptomyces avermitilis MA5508 by exposure to ultra-violet irradiation for 45 minutes. Selection was on the basis of the production of melanoid pigments aerial mycelium and sporulation on yeast extract malt extract agar and non-production of avermectin.

General growth characteristics-Good growth on glycerol asparagin agar, yeast malt extract agar, inorganic salt starch agar, peptone iron agar and oatmeal agar. Sparse growth on tap water agar. Culture also grows well in trytone yeast extract broth.

Colony morphology-Substrate mycelium is greenish-white to light gray-olive. Aerial mycelium white to light gray olive. Spore mass, when present, is greenish-white to very pale green. Colonies are rough textured and leathery.

Micromorphology-Aerial mycelium (0.76–1.0 µm dia.) arises from a substrate mycelium and is branched and flexous. In mature cultures, the aerial mycelium commonly terminates in chains of spores arranged in compact spirals with a loop width of approximately 1.14 µm diameter. On glycerol asparagine agar sporophores are observed in both sprials and primitive loops (retinaculum spertum).

Miscellaneous physiological reactions-Culture produces melanoid pigments in tryptone yeast extract broth, $H_2S$ in peptone-iron agar. Carbon source utilization pattern is as follows: good utilization of cellobiose, glucose; fair utilization fructose, D-manitol, D-mannose, L-rhamnose; poor utilization of D-arabinose, L-arabinose, inositol, α-D-lactose, β-D-lactose, D-maltose, D-xylose; no utilization of D-raffinose, sucrose, L-xylose.

| | Cultural characteristics of Streptomyces avermitilis MA6078 at 21 days | | | |
| --- | --- | --- | --- | --- |
| | Amount of Aerial Mycelium | | Soluble | Reverse |
| Medium | Growth | and/or Spores | Pigments | Color |
| Yeast Extract Malt Extract | good | Aerial mycelium greenish white (153) Spira spore chains | none noted | light gray olive (109) |

| Cultural characteristics of Streptomyces avermitilis MA6078 at 21 days | | | | |
|---|---|---|---|---|
| | Amount of Aerial Mycelium | | Soluble | Reverse |
| Medium | Growth | and/or Spores | Pigments | Color |
| Glucose Asparagine | good | Aerial mycelium yellow white (92) Spore chains present in sprials and primitive loops (RA) | none noted | pale yellow green (121) |
| Inorganic Salts Starch | good | Aerial mycelium pale green (149) | none noted | gray olive green (127) |
| Oatmeal | good | Aerial mycelium white (263) | none noted | pale green yellow (104) |
| Tap Water | sparse | white | none noted | white |
| Peptone Iron | good | | black (within 24h pi) | |

| Carbohydrate utilization pattern of Streptomyces avermitilis MA6078 at 21 days | |
|---|---|
| Carbon Source | Utilization |
| D-arabinose | 1 |
| L-arabinose | 1 |
| cellobiose | 3 |
| D-fructose | 2 |
| inositol | 1 |
| α-D-lactose | 1 |
| β-D-lactose | 1 |
| D-maltose | 1 |
| D-mannitol | 2 |
| D-mannose | 1 |
| D-raffinose | 0 |
| L-rhamnose | 2 |
| sucrose | 0 |
| D-xylose | 1 |
| L-xylose | 0 |
| a-D-gluose (control) | 3 |

3 = good utilization
2 = moderate utilization
1 = poor utilization
0 = no utilization Diagnosis-The morphological characteristics of this strain compares favorably with the published description of Streptomyces avermtilis MA4680 (Burg et. al. Antimicrob. Agents Chemother. 15: 361–367). Differences in carbohydrate utilization patterns were observed, most notably the inability of MA6078 to utilize raffinose and sucrose. In addition, MA6078 was not found to produce abundant melanoid pigments on yeast extract malt extract, glucose aspargine or oatmeal agar.

The mono- and disaccharide compounds are prepared by fermenting the following compound in a culture medium of Streptomyces avermitilis which is incapable of producing avermectin compounds in the absence of such compound:

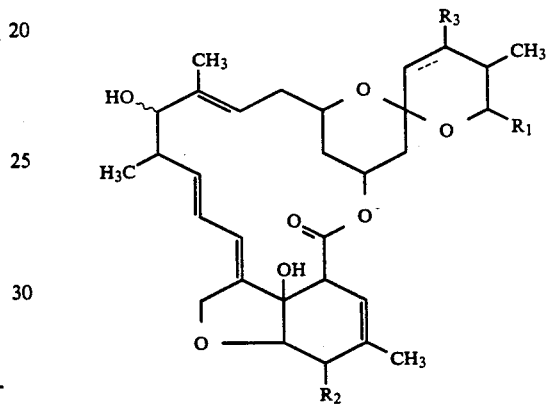

wherein
$R_1$ is alkyl of from 1 to 8 carbon atoms, alkenyl of from 2 to 8 carbon atoms or cycloalkyl of from 3 to 8 carbon atoms;
$R_2$ is hydroxy, methoxy, keto or acetoxy;
$R_3$ is hydrogen, hydroxy oxo, or hydroxyimino; and
the broken line indicates a single or a double bond at the 22,23-position and $R_3$ is present only when the broken line indicates a 22,23-single bond.

The fermentation is carried out in a medium containing S. avermitilis MA-6078 and produces the following compound:

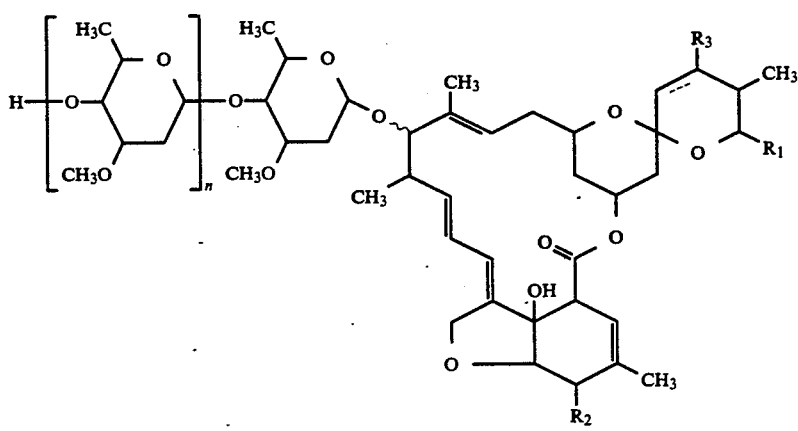

where $R_1$, $R_2$, $R_3$ and the broken line are as defined above and n is 0 or 1, when the $C_{13}$ carbon-oxygen bond is below the plane of the ring ($\alpha$) or n is O when the $C_{13}$ carbon-oxygen bond is above the plane of the ring ($\beta$).

The microorganism has the characteristic of glycosylating only with the $\alpha$-L-oleandrose sugar moiety which is the same sugar moiety as is found in the natural product avermectin molecules, although S. avermitilis MA-6078 is incapable of preparing avermectin compounds in fermentations which do not involve the addition of an avermectin aglycone substrate.

In addition, with certain avermectin aglycone substrate molecules, the fermentation is seen to result in the addition of a methyl group at the 5-position hydroxy group. That is, the 5-hydroxy is converted into a 5-methoxy. However, it is also readily possible to synthetically produce the 5-methoxy compounds from the 5-hydroxy compounds by following the procedure of Mrozik et. al. in *J. Org. Chem.* 51 pg. 3508 (1986) and such compounds are included within the ambit of the instant invention.

Certain of the compounds prepared by the process of the instant invention have not previously been described and thus are novel compounds. These compounds are within the scope of this invention.

5-Methoxy,13-β-22-23 dihydro avermectin $B_{1}a$ monosaccharide where $R_1$ is sec-butyl, $R_2$ is methoxyl, $R_3$ is hydrogen and n is 0.

5-Methoxy,13-β-avermectin $B_{1}a$ monosaccharide where $R_1$ is sec-butyl, $R_2$ is methoxyl, $R_3$ is absent and n is 0.

5-Methoxy,13-β-avermectin $B_{1}b$ monosaccharide where $R_1$ is isopropyl, $R_2$ is methoxyl, $R_3$ is absent and n is 0.

5-Methoxy,13-β-22-23 dihydro avermectin $B_{1}b$ monosaccharide where $R_1$ is isopropyl, $R_2$ is methoxyl, $R_3$ is hydrogen and n is 0.

5-Methoxy,13-β-avermectin $B_{2}a$ monosaccharide where $R_1$ is sec-butyl, $R_2$ is methoxyl, $R_3$ is hydroxyl and n is 0.

5-Acetyl,13-β-avermectin $B_{1}a$ monosaccharide where $R_1$ is sec-butyl, $R_2$ is acetyl, $R_3$ is absent and n is 0

5-Acetyl,13-β-22-23 dihydro avermectin $B_{1}a$ monosaccharide where $R_1$ is sec-butyl, $R_2$ is acetyl, $R_3$ is hydrogen and n is 0.

5-Acetyl,13-β-avermectin $B_{2}a$ monosaccharide where $R_1$ is sec-butyl, $R_2$ is acetyl, $R_3$ is hydroxyl and n is 0.

The instant compounds are produced during the aerobic fermentation of suitable aqueous nutrient media under conditions described hereinafter, with a producing strain of *Streptomyces avermitilis* MA-6078, ATCC 55017. Aqueous media such as those used for the production of many antibiotic substances are suitable for use in the process for the production of these macrocyclic compounds.

Such nutrient media contain sources of carbon and nitrogen assimilable by the microorganism and generally low levels of inorganic salts. In addition, the fermentation media may contain traces of metals necessary for the growth of the microorganisms, and production of the desired compound. These are usually present in sufficient concentrations in the complex sources of carbon and nitrogen, which may be used as nutrient sources, but can, of course, be added separately to the medium if desired.

In general, carbohydrates such as sugars, for example dextrose, maltose, lactose, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount of carbohydrate between 1 and 100 g/l in the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by *Streptomyces avermitilis* MA-6078, ATCC 55017 in the production of the instant compounds. The various sources of nitrogen can be used alone or in combination in amounts ranging from 1 to 5 g/l in the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, and the like.

It should be noted that the media described hereinbelow and in the Examples are merely illustrative of the wide variety of media, which may be employed, and are not intended to be limitative.

The following are Examples of media suitable for growing strains of *Streptomyces avermitilis* MA-6078, ATCC 55017:

| Composition of Media | |
|---|---|
| Medium 1 | |
| Dextrose | 20 g. |
| Peptone | 5 g. |
| Meat Extract | 5 g. |
| Primary Yeast | 3 g. |
| NaCl | 5 g. |
| $CaCO_3$ (after pH adjustment) | 3 g. |
| Distilled Water | 1000 ml. |
| pH 7.0 | |
| Medium 2 | |
| Tomato Paste | 20 g. |
| Modified Starch (CPC) | 20 g. |
| Primary Yeast | 10 g. |
| $CoCl_26H_2O$ | 0.005 g. |
| Distilled Water | 1000 ml. |
| pH 7.2–7.4 | |
| Medium 3 (Slant Medium) | |
| Dextrose | 10.0 g. |
| Bacto Asparagine | 0.5 g. |
| $K_2HPO_4$ | 0.5 g. |
| Bacto Agar | 15.0 g. |
| Distilled Water | 1000 ml. |
| pH 7.0 | |
| Medium 4 (Seed Medium) | |
| Soluble Starch | 10.0 g. |
| Ardamine pH | 5.0 g. |
| NZ Amine E | 5.0 g. |
| Beef Extract | 3.0 g. |
| $MgSO_47H_2O$ | 0.5 g |
| Cerelose | 1.0 g. |
| $Na_2HPO_4$ | 0.190 g. |
| $KH_2PO_4$ | 0.182 g. |
| $CaCO_3$ | 0.5 g. |
| Distilled Water | 1000 ml. |
| pH 7.0–7.2 | |
| Medium 5 | |
| Tomato Paste | 40.0 g. |
| Oat Flour | 10.0 g. |
| Cerelose | 10.0 g. |
| Corn Steep Liquor | 5.0 g. |
| Trace Element Mix | 10.0 ml. |
| Distilled Water | 1000 ml. |

| Composition of Media | |
|---|---|
| pH 6.8 | |
| Trace Element Mix | 1000 ml. |
| FeSO$_4$.7H$_2$O | 1000 mg |
| MnSO$_4$.4H$_2$O | 1000 mg. |
| CuCl$_2$.2H$_2$O | 25.0 g. |
| CaCl$_2$ | 100.0 mg. |
| H$_2$BO$_3$ | 56.0 mg. |
| (NH$_4$)$_2$MoO$_4$.4H$_2$O | 10.0 mg. |
| ZnSO$_4$.7H$_2$O | 200.0 mg. |
| Distilled Water | 1000 ml. |
| pH | |
| Medium 6 | |
| CPC Industrial Starch Modified (Available from CPC Corp.) | 40.0 g. |
| Distiller's Solubles | 7.0 g. |
| Autolyzed Yeast (Ardamine pH available from Yeast Products Inc.) | 5.0 g. |
| CoCl$_2$.6H$_2$O | 50.0 mg. |
| Distilled Water | 1000 ml. |
| pH 7.3 | |

The fermentation employing *Streptomyces avermitilis*, MA-6078 ATCC 55017 can be conducted at temperatures ranging from about 20° C. to about 40° C. For optimum results, it is most convenient to conduct these fermentations at a temperature in the range of from about 24° C. to about 30° C. Temperatures of about 27°-28° C. are most preferred. The pH of the nutrient medium suitable for producing the instant compounds can vary from about 5.0 to 8.5 with a preferred range of from about 6.0 to 7.5.

The avermectin aglycone compounds are added to the fermentation of *Streptomyces avermitilis* MA-6078 in quantities of from 0.1 to 1.0 g per liter of fermentation medium. It is preferred to use from 0.1 to 0.5 g per liter. The avermectin aglycone compound may be added at any time during the fermentation cycle. The compounds may be added to the medium ingredients before the culture is added and the fermentation begins or they may be added during the course of the fermentation. In order that the cultures have sufficient time to effect the biotransformation, it is preferred that the avermectin aglycone compounds be added to the fermentation before 50% of the cycle is completed, preferably before 25% of the cycle is completed.

Small scale fermentations are conveniently carried out by placing suitable quantities of nutrient medium in a flask employing known sterile techniques, inoculating the flask with either spores or vegetative cellular growth of *Streptomyces avermitilis* MA-6078, ATCC 55017, loosely stoppering the flask with cotton and permitting the fermentation to proceed in a constant room temperature of about 28° C. on a rotary shaker at from 95 to 300 rpm for about 2 to 10 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of *Streptomyces avermitilis* MA-6078. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 300 rpm and about 50 to 500 liters per minute (LPM) of air.

The separation of the novel compound from the whole fermentation broth and the recovery of said compounds is carried out by solvent extraction and application of chromatographic fractionations with various chromatographic techniques and solvent systems.

The instant compounds have slight solubility in water, but are soluble in organic solvents. This property may be conveniently employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extractions are desirable to achieve maximum recovery. The solvent removes the instant compound as well as other substances lacking the antiparasitic activity of the instant compound. If the solvent is a water immiscible one, the layers are separated and the organic solvent is evaporated under reduced pressure. The residue is placed onto a chromatography column containing preferably, silica gel. The column retains the desired products and some impurities, but lets many of the impurities, particularly the nonpolar impurities, pass through. The column is washed with a moderately polar organic solvent such as methylene chloride or chloroform to further remove impurities, and is then washed with a mixture of methylene chloride or chloroform and an organic solvent of which acetone, methanol, and ethanol and the like are preferred. The solvent is evaporated and the residue further chromatographed using column chromatography, thin layer chromatography, preparative thin layer chromatography, high pressure liquid chromatography and the like, with silica gel, aluminum oxide, ion exchange resins, dextran gels and the like, as the chromatographic medium, with various solvents and combinations of solvents as the eluent. Thin layer, high pressure, liquid and preparative layer chromatography may be employed to detect the presence of, and to isolate the instant compounds. The use of the foregoing techniques as well as others known to those skilled in the art, will afford purified compositions containing the instant compounds. The presence of the desired compounds is determined by analyzing the various chromatographic fractions for biological activity of physico-chemical characteristics. The structures of the instant compounds have been determined by detailed analysis of the various spectral characteristics of the compounds, in particular their nuclear magnetic resonance, mass, ultraviolet and infrared spectra.

The compounds of this invention have significant parasiticidal activity as anthelmintics, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Stongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attach primarily the intestinal tract while others, such as Haemonchus and Ostertagia, are more prevalent in the stomach while others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compounds are also useful against parasites which infect humans. The most common genera of parasites of the gastro-intestinal tract of parasites of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp. and the housefly *Musca domestica*.

The compounds are also useful against insect pests of stored grains such as Tribolium sp., Tenebrio sp. and of agricultural plants such as spider mites, (Tetranychus sp.), aphids, (Acyrthiosiphon migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or dicalcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium sterate, vegetable gums and the like. Such unit dosage formulations may be varied widely with respect to their total weight and constant of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol, formal and aqueous parenteral formulations are also used. The active compound or compounds are dissolved or suspended in the parenteral formulation for administration; such formulations generally contain from 0.55 to 5% by weight of the active compound.

Although the antiparasitic agents of this invention find their primary use in the treatment and/or prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection of infestation. Generally, good results are obtained with our novel compounds by the oral administration of from about 0.001 to 10 mg per kg of animal body weight, such total dose being given at one time or in divided doses over a relatively short period of time such as 1–5 days. With the preferred compounds of the invention, excellent control of such parasites is obtained in animals by administering from about 0.025 to 0.5 mg per kg of body weight in a single dose. Repeat treatments are given are required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution of blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired antiparasitic result.

In using the compounds of this invention, the individual components may be isolated and purified and used in that form. Alternatively, mixtures more of the individual components may be used. It is not necessary to completely separate the various compounds obtained from the purification of the fermentation broth. Generally, there is obtained a mixture containing two or more of the compounds, but having other unrelated compounds excluded therefrom, and such mixture may be used for the prevention and treatment of parasitic diseases as described herein. Such a mixture generally will contain unequal proportions of the compounds, however, all of the compounds have substantial activity and the antiparasitic activity of the mixture can be accurately determined.

In addition, where the compounds are to be added to an animal's feed, it is possible to utilize the dried mycelial cake from the fermentation broth. The mycelia contain a preponderance of the activity and since the level of the activity of the mycelia can be determined, it can be added directly to the animal's feed.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The anthelmintic activity of the instant compounds may be determined by orally administering via the feed, a sample of the individual compound, a mixture of such compounds, a concentrated extract, and the like to a mouse which had been infected 3 days earlier with a gastrointestinal parasite. At 11, 12 and 13 days after the initiation of the medication, the feces of the mouse are examined for eggs, and on the next day the mouse is sacrificed and the number of worms present in the proximal portion of the small intestine are determined. An active compound is observed when there is a significant reduction of egg and worm counts when compared to infected, unmedicated controls.

The following examples are being provided in order that the instant invention may be more fully understood. Such examples are not to be construed as being limitative of the invention.

GENERAL PROCEDURE

Organisms

MA-6078, ATCC 55017 is a mutant of *S. avermitilis* which does not produce avermectins.

Media

Seed media contained the following in g per liter: yeast extract (Difco), 20; Hycase S.F, 20; dextrose, 20 g, $KNO_3$, 2.0; NaCl, 0.5; $MnSO_4.H_2O$, 0.005; $ZnSO_4.7H_2O$, 0.01; $Ca Cl_2.2H_2O$, 0.02; $Fe SO_4.7H_2O$, 0.025. The pH was adjusted to 7.0.

Production media contained the following in g per liter: Peptonized milk, 17.5; Ardamine pH, 2.75; dextrose, 75; $CuSO_4.5H_2O$, 0.00006; $ZnSO_4.7H_2O$, 0.001; $CoCl_2.6H_2O$, 0.0001; $FeCl_3.6H_2O$, 0.003; $MgSO_4.7H_2O$, 0.5. The pH was adjusted to 7.2.

Inoculum Preparation

Frozen vegetative mycelia (FVM) were prepared by inoculating 250 ml seed medium in a 2 liter 3 baffle flask and incubating at 27° C., 85% relative humidity and 200 RPM for 16 hours. The packed cell volume of the culture was 15% and the pH 5.7-6.4. Aliquots of the culture were frozen and used as source of inoculum for future experiments.

Seed Culture

To 25 ml of seed medium in a 250 ml 3 baffle flask, 1.0 ml of FVM was added as inoculum and the flasks were incubated at 30° C., 85% relative humidity and 200 RPM for 16 hours.

Biotransformation and Isolation

To 22.5 ml of production media, 1.0 ml of seed culture was added and flasks were incubated at 27° C., 85% relative humidity at 200 RPM for 48 hours. 1.3-3.0 mg of avermectin aglycone in 0.05 ml DMSO were added and the flasks were incubated for 5 days at 27° C., 85% relative humidity and 220 RPM. Each flask was extracted with 50 ml portions of $CH_2Cl_2$. The $CH_2Cl_2$ extracts were combined and concentrated. The avermectin monosaccharide and disaccharide were isolated by HPLC on Dupont Zorbax ODS column using $CH_2OH:H_2O$ (85:15) as the mobile phase. The structures of the purified avermectins were determined by mass spectroscopy and NMR spectroscopy.

SPECIFIC EXAMPLES

The following avermectin aglycones have been glycosylated.

EXAMPLE 1

13α-hydroxy-22, 23-dihydro avermectin $B_1a$ aglycone→5-methoxy-13α-22,23-dihydro avermectin $B_1a$ (a disaccharide).

EXAMPLE 2

13α-hydroxy-22,23-dihydro avermectin $B_1b$ aglycone→5-methoxy-13α-22,23-dihydro avermectin $B_1b$ (a disaccharide).

EXAMPLE 3

13α-hydroxy-avermectin-$B_2a$ aglycone→13α-avermectin $A_2a$ (a disaccharide).

EXAMPLE 4

5-keto-13α-hydroxy avermectin $B_2a$ aglycone→5-methoxy-13α-avermectin $B_2a$ (a disaccharide).

EXAMPLE 5

13α-avermectin $A_{2a}$ aglycone→13α-avermectin $A_{2a}$ (a disaccharide).

EXAMPLE 6

13α-avermectin $A_{1a}$ aglycone→13α-avermectin $A_{1a}$ (a dissacharide).

EXAMPLE 7

13β-22,23-dihydro avermectin $B_{1a}$ aglycone→5-methoxy-13β-22,23-dihydro avermectin $B_{1a}$ monosaccharide.

EXAMPLE 8

13β-avermectin $B_{2a}$ aglycone→5-methoxy-13β-avermectin $B_{2a}$ monosaccharide.

EXAMPLE 9

13β-avermectin $B_{1a}$ aglycone→5-methoxy-13β-avermectin $B_{1a}$ monosaccharide.

EXAMPLE 10

5-Acetyl-13β-avermectin $B_{1a}$ aglycone→5-acetyl-13β-avermectin $B_{1a}$ monosaccharide.

EXAMPLE 11

5-Acetyl-13β-avermectin $B_{2a}$ aglycone→5-acetyl-13β-avermectin $B_{2a}$ monosaccharide.

EXAMPLE 12

5-Acetyl-22,23-dihydro-13β-avermectin $B_{1a}$ aglycone→5-acetyl-22,23-dihydro-13β-avermectin monosaccharide.

What is claimed is:

1. A process for the conversion of avermectin aglycone molecules into mono α-L-oleandrose or di-α-L-oleandrose glycoslated derivatives thereof which comprises adding an avermectin aglycone substrate to the fermentation medium of a mutant strain of *Streptomyces avermitilis* which is incapable of preparing avermectin molecules in the absence of the added avermectin aglycone substrate.

2. The process of claim 1 where the avermectin aglycone substrate has the following structure:

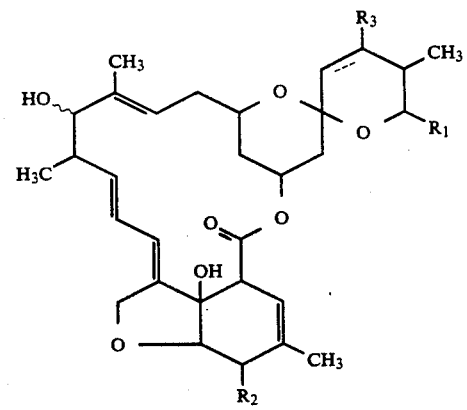

wherein
$R_1$ is alkyl of from 1 to 8 carbon atoms or alkenyl of from 2 to 8 carbon atoms or cycloalkyl of from 3 to 8 carbon atoms;
$R_2$ is hydroxy, methoxy, keto or acetoxy;
$R_3$ is hydrogen, hydroxy, oxo or hydroxyimino; and the broken line indicates a single or a double bond at the 22,23-position and $R_3$ is present only when the broken line indicates a 22,23-single bond and the product of the process has the following structure:

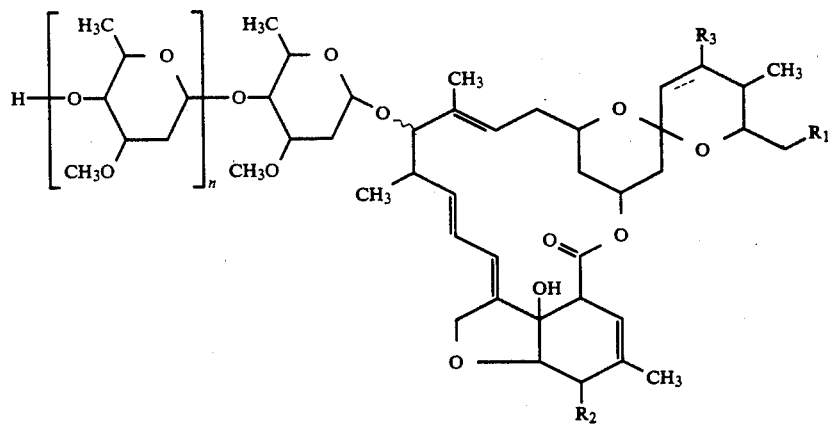

wherein $R_1$, $R_2$, $R_3$ and the broken line are as defined above and n is 0 or 1, when the $C_{13}$ carbon-oxygen bond is below the plane of the ring (α) or n is 0 when the $C_{13}$ carbon-oxygen bond is above the plane of the ring (β).

3. The process of claim 1 where the *Streptomyces avermitilis* microorganism is MA-6078, ATCC 55017.

4. The process of claim 1 where both the mono-oleandrose and di-oleandrose derivatives are formed when the $C_{13}$-carbon-oxygen bond is equatorial (α) and where mono-oleandrose derivatives are formed when the $C_{13}$ carbon-oxygen bond is axial (β).

5. The process of claim 1 wherein the substrate is added to the extent of from 0.1 to 1.0 g per liter of fermentation medium.

6. The process of claim 5 wherein the substrate is added to the extent of from 0.1 to 0.5 g per liter.

7. The process of claim 1 wherein the sources of carbon are present in the form of carbohydrate.

8. The process of claim 7 wherein the sources of carbohydrate is present to the extent from 1 to 100 g per liter of the fermentation medium.

9. The process of claim 1 wherein the source of nitrogen is present at from 5 to 10 g per liter of the fermentation medium.

10. The process of claim 1 wherein the fermentation is carried out at from 20° to 40° C. and a pH from 5.0 to 8.5.

11. The process of claim 10 wherein the fermentation is carried out at from 24° C. to 30° C. and a pH of from 6.0 to 7.5.

12. The process of claim 11 wherein the fermentation is carried out at from 27° to 28° C.

13. The process of claim 1 wherein the substrate is added to the fermentation broth before 50% of the fermentation cycle is completed.

14. The process of claim 13 wherein the substrate is added to the fermentation broth before 25% of the fermentation cycle is completed.

* * * * *